United States Patent
Chen et al.

(10) Patent No.: US 9,051,330 B2
(45) Date of Patent: Jun. 9, 2015

(54) DITHIOLOPYRROLONES WITH THERAPEUTIC ACTIVITY

(75) Inventors: Genhui Chen, Burnaby (CA); Jianxiong Li, Port Moody (CA); John Webster, North Vancouver (CA); Bin Li, Burnaby (CA)

(73) Assignee: Welichem Biotech Inc., Burnaby (CA)

( * ) Notice: Subject to any disclaimer, the term of this patent is extended or adjusted under 35 U.S.C. 154(b) by 944 days.

(21) Appl. No.: 10/509,074

(22) PCT Filed: Mar. 18, 2003

(86) PCT No.: PCT/CA03/00380
§ 371 (c)(1), (2), (4) Date: Oct. 14, 2005

(87) PCT Pub. No.: WO03/080624
PCT Pub. Date: Oct. 2, 2003

(65) Prior Publication Data
US 2006/0074125 A1  Apr. 6, 2006

Related U.S. Application Data

(60) Provisional application No. 60/367,265, filed on Mar. 26, 2002, provisional application No. 60/418,698, filed on Oct. 17, 2002.

(51) Int. Cl.
*A61K 31/407* (2006.01)
*C07D 495/04* (2006.01)

(52) U.S. Cl.
CPC .................................. *C07D 495/04* (2013.01)

(58) Field of Classification Search
USPC ............................ 514/412; 548/453; 544/242
See application file for complete search history.

(56) References Cited

U.S. PATENT DOCUMENTS

| | | | | |
|---|---|---|---|---|
| 2,752,359 A * | 6/1956 | Celmer | ......................... | 548/453 |
| 2,776,967 A * | 1/1957 | Hogg et al. | ...................... | 540/29 |
| 2,798,811 A * | 7/1957 | Bockelmann et al. | ...... | 426/330.4 |
| 3,038,819 A * | 6/1962 | Ross et al. | ..................... | 427/384 |
| 3,057,779 A * | 10/1962 | Shay et al. | .................... | 424/117 |
| 5,827,872 A * | 10/1998 | Webster et al. | ............... | 514/421 |
| 6,020,360 A * | 2/2000 | Webster et al. | ............... | 514/421 |
| 6,583,171 B1 * | 6/2003 | Webster et al. | ............... | 514/421 |
| 8,071,637 B2 * | 12/2011 | Guo et al. | ..................... | 514/412 |

FOREIGN PATENT DOCUMENTS

| | | |
|---|---|---|
| GB | 2170498 A | 8/1986 |
| GB | 2173499 A | 10/1986 |
| JP | 63112586 A | 5/2009 |
| WO | 9428001 A1 | 12/1994 |
| WO | 9505384 A1 | 2/1995 |
| WO | 9912543 A1 | 3/1999 |

OTHER PUBLICATIONS

Webster et al. (AN 2000:83116 ZCAPLUS, DN 132:93329, abstract of US 6020360).*
Webster et al. (AN 19999:193997, Zcaplus, abstract WO 9912543, Dithiolopyrrolones and their corresponding monoxides and dioxides as antineoplastic agents from *Xenorhabdus bovienii*, US equivalent 6583171).*
Bhate, D.S. and Y.M. Sambray, "Synthetic thiolutin analogues", Hindustan Antibiotics Bulletin, 6(1):17-18, 1963.
Celmer, Walter D., et al. "A common hydrolysis product of thiolutin and aureothricin", Antibiotics Ann, 1953-54, Proc Symposium Antibiotics (Washington D.C.), 1953, pp. 622-625.
Hagio, Katsuaki, et al., "Total syntheses of holomycin, thiolutin, and aureothricin", Bulletin of the Chemical Society of Japan, 47(6):1484-1489, 1974.
Lamari, L., et al. "New dithiolopyrrolone antibiotics from saccharothrix sp. SA 233, I. taxonomy, fermentation, isolation and biological activities", J Antibiotics, 55(8): 696-701, 2002.
Monks, A. et al. "Feasability of high-flux anticancer drug screen using a diverse panel of cultured human tumor cell lines", J Natl Cancer Inst, 83(11):757-766, Jun. 5, 1991.
Sharma, Sheela, et al. "Screening of potential chemopreventive agents using biochemical markers of carcinogenesis", Cancer Research, 1994, 54, 5848-5855.
McInerney, Bernie V., et al., "Biologically active metabolites from *Xenorhabdus* Spp., Part 1. Dithiolopyrrolone derivatives with antibiotic activity", Journal of Natural Products, 1991, 54(3):774-784.

* cited by examiner

*Primary Examiner* — Sabiha N Qazi
(74) *Attorney, Agent, or Firm* — Oyen Wiggsl Green & Mutala LLP

(57) ABSTRACT

The present invention provides novel dithiolopyrrolone compounds and their salts, which are useful as treatments for cancer and other proliferative diseases. The present invention also provides therapeutic compositions comprising particularly useful types of dithiolopyrrolones, the salts thereof, and methods of using the compounds within such types, particularly in treating proliferative diseases such as cancer.

6 Claims, No Drawings

DITHIOLOPYRROLONES WITH THERAPEUTIC ACTIVITY

This application is the U.S. National Stage of International Application No. PCT/CA03/00380, which has an International Filing Date of Mar. 18, 2003, published in English on Oct. 2, 2003, as WO 03/080624, and which is hereby incorporated by reference in its entirety. This application claims benefit, under 35 U.S.C. §119(e), of U.S. Provisional Application No. 60/367,265, filed Mar. 26, 2002, and U.S. Provisional Application No. 60/418,698, filed Oct. 17, 2002, each of which is incorporated by reference herein in its entirety.

DESCRIPTION OF THE INVENTION

The present invention provides novel dithiolopyrrolone compounds and their salts, which are useful as treatments for cancer and other proliferative diseases. The present invention also provides therapeutic compositions comprising particularly useful types of dithiolopyrrolones, the salts thereof, and methods of using the compounds within such types, particularly in treating proliferative diseases such as cancer.

BACKGROUND OF THE INVENTION

Cancer is one of the major causes of death in humans and animals. Millions of people in the world are diagnosed every year as having cancer and a large proportion of these people die of cancer. Despite extensive worldwide effort over many years, cancers continue to be hard-to-treat diseases, and there is an urgent need for more effective anticancer drugs.

Dithiolopyrrolones are a group of compounds with 1,2-dithiolo[4,3-b]pyrrol-5(4H)-one ring. The substitutes attached to the ring, particularly at position 2 and 6, lead to diverse subgroups of derivatives with different structural features and bioactivities. Compounds bearing this basic structural feature have been known in the art. Natural dithiolopyrrolones have been shown to have activities against microorganisms as well as other activities such as chemopreventive (Sharma et al., 1994) and anticancer (U.S. Pat. No. 6,020,360, WO 99/12543 both of Webster et. al.). Certain synthetic dithiolopyrrolones and their antimicrobial activities have been disclosed (D. S. Bhate & Y. M. Sambray, 1963. Hindustan, *Antibiotic Bulletin* 6(1): 17-18; Katsuaki Hagio et al. *Bull. Chem. Soc. Jpn* 1974, 47, 1484-1489; Broom, et al. WO 9505384 and Godfrey & Dell, GB2170498).

The present invention relates to certain new types of dithiolopyrrolones and particular specific dithiolopyrrolones that have been found to have particular use in the treatment of cancers. The invention relates to such types and particular compounds as new chemical compounds, and also to pharmaceutical compositions containing them and methods for the treatment of disease using them.

In addition, and more generally, such types of dithiolopyrrolones and particular specific dithiolopyrrolones are found to be useful against proliferative diseases in general. Proliferative diseases are, but are not limited to, disorders wherein unwanted cell proliferation of one or more subset(s) of cells in a multicellular organism occurs, resulting in harm (e.g., discomfort or decreased life expectancy) to the multicellular organism. Proliferative diseases can occur in different types of animals and in humans. Proliferative diseases include leukemia and blood vessel proliferative disorders, and fibrotic disorders such as cancers, tumors, hyperplasias, fibrosis (especially pulmonary fibrosis, but also other kinds of fibrosis, such as renal fibrosis), angiogenesis, psoriasis, arteriosclerosis and smooth muscle cell proliferation in the blood vessels, such as stenosis or restenosis following angioplasty.

SUMMARY OF THE INVENTION

In one aspect the invention provides methods and compositions for treating proliferative diseases, such as cancer and psoriasis, comprising administrating to a subject in need of such treatment, an effective amount of a compound of one of the structures shown below. In another aspect, the invention deals with pharmaceutical compositions containing compounds of the structures shown below, for the treatment of proliferative diseases, and especially cancer. In another aspect, the invention includes, as new chemical compounds, those compounds of the structures shown below are not previously disclosed.

The structures of compounds according to the invention are the following:

(a). Compounds of the following formula (formula I)

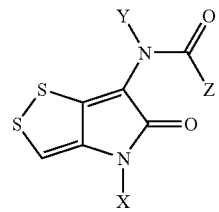

wherein Z=aryl, heterocyclic, substituted or unsubstituted alkenyl, substituted or unsubstituted alkynyl group, while X and the same Y can be the same or different, are hydrogen, substituted or unsubstituted alkyl, cycloalkyl, aryl, aralkyl or heterocyclic group, except the chemicals with:

Z=phenyl, Y=H, X=H, methyl, benzyl and Z=4-pyridine, X=methyl, Y=H; or wherein X=aryl, heterocyclic, Y and Z, can be the same or different, are hydrogen, unsubstituted or substituted or alkyl of two or less hydroxyl groups and no carboxylic acid group, cycloalkyl, aryl, aralkyl or heterocyclic group, except the chemicals with:

Z=methyl, Y=H, X=phenyl, 4-methoxyphenyl, 4-methylphenyl.

(b) Compounds of the following formula (formula II)

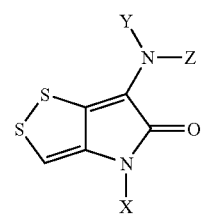

wherein X, Y and Z can be the same or different, is hydrogen, substituted or unsubstituted alkyl, cycloalkyl, aryl, aralkyl or heterocyclic group, except that when X=Y=Z=methyl and when X=H, Y=Z=methyl.

In particular, the following group of compounds that are of the above (a):

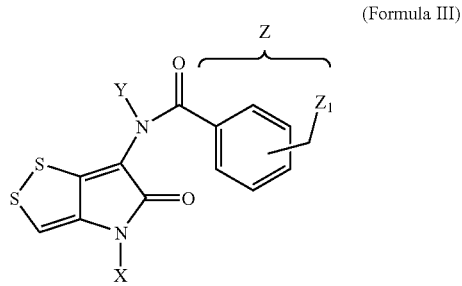

(Formula III)

wherein X and Y can be the same or different, are hydrogen, substituted or unsubstituted alkyl, cycloalkyl, aryl or aralkyl group. $Z_1$ is a group with at lest two hydrophilic atoms selected from N or O, such as piperazinyl, 4-methyl-piperazinyl and morpholinyl. The position of —$CH_2$-Z group can be at ortho, meso or para on the benzene ring.

In this disclosure, dithiolopyrrolones within the Formulae I, II and III are referred to as "types of dithiolopyrrolones" according to the invention or by similar wording, and individual compounds disclosed herein are referred to by the wording "specific dithiolopyrrolones", "specific compounds", "particular compounds" or "compounds of the invention" or by similar wording.

DETAILED DESCRIPTION OF THE INVENTION

In this invention, it is discovered that different substitutes have great, unpredictable effects on the overall anticancer properties of different dithiolopyrrolones. It was discovered that introduction of water-soluble groups, such as carboxyl group, polyhydroxyl groups (such as a sugar unit) drastically reduced the anticancer activity of the corresponding, unsubstituted compounds. However, another newly designed group of compounds, together with the introduction of water-soluble groups, have not only significantly improved solubility in water, but surprisingly, they provide enhanced anticancer activity of the corresponding, unsubstituted compounds. This unexpected discovery is described in this invention, and allows us to invent different types of dithiolopyrrolones.

The types of dithiolopyrrolones and specific dithiolopyrrolones of the subject invention are prepared by the methods described below together with the structure of each dithiolopyrrolone compound for which structural information is given and has been confirmed by its NMR and MS spectroscopy.

Skilled chemists will be able to use procedures as disclosed herein and others to produce these types of dithiolopyrrolones and specific dithiolopyrrolones from commercially available stock substances. In carrying out such operations, any suitable filtration, chromatographic, and other purification techniques might be employed by those skilled in the art. A more complete understanding of the invention can be obtained by reference to preferred embodiments of the invention, which are illustrated by the following specific examples and methods of the invention. It will be apparent to those skilled in the art that the examples involve use of materials and reagents that are commercially available from chemical companies, so no details are given respecting them.

Dithiolopyrrolones form salts, therefore, the compounds of the invention and types of dithiolopyrrolones of the invention include the salts of the compounds disclosed herein and the types of dithiolopyrrolones disclosed herein. The term "salts", as used herein, denotes acidic and/or basic salts, formed with inorganic and/or organic acids and bases. Suitable acids include, for example, hydrochloric, sulfuric, nitric, benzenesulfonic, acetic, maleic, tartaric and the like, which are pharmaceutically acceptable. While pharmaceutically acceptable salts are preferred, particularly when employing the compounds of the invention as medicaments, other salts find utility, for example, in the production of these compounds, or where non-medicament-type uses are contemplated.

The types of dithiolopyrrolones and the particular compounds disclosed herein have strong antiproliferative activity, in particular, strong activity against a wide range of human cancer cell lines and especially in the treatment of malignant mammary cells. Importantly, they inhibit the growth of leukemia, lung, melanoma, colon, CSN, renal, prostate, ovarian and breast cancer cell lines. They are also useful against other proliferative diseases, including blood vessel proliferative disorders, and fibrotic disorders such as cancers, tumors, hyperplasias, fibrosis (especially pulmonary fibrosis, but also other kinds of fibrosis, such as renal fibrosis), angiogenesis, psoriasis, atherosclerosis and smooth muscle cell proliferation in the blood vessels, such as stenosis or restenosis following angioplasty.

The present invention provides methods of treating a mammal affected by cancers or other proliferative diseases sensitive to the particular compounds and types of dithiolopyrrolones, which comprises administering to the affected individual a therapeutically effective amount of one of the specific compounds or a compound selected from the disclosed types of dithiolopyrrolones, a salt thereof or a pharmaceutical composition thereof. In particular, the compounds and the salts thereof of the invention may be used to treat mammalian cancers, and other proliferative diseases. The present invention also relates to the pharmaceutical compositions which contain an active ingredient of these compounds or a pharmaceutically acceptable salt thereof, or a compound or pharmaceutically acceptable salt selected from a type of dithiolopyrrolone of the invention, as well as the process for the preparation of such a pharmaceutical composition.

Examples of pharmaceutical compositions include any solid (tablets, pills, capsules, granules, powder etc.) or liquid (solutions, suspensions or emulsions) in a suitable composition for oral, topical or parenteral administration. These formulations may contain the pure compound or be in combination with a carrier or some other pharmaceutically active compound. These compositions may need to be sterile when administered parenterally.

The administration of the disclosed compounds of the invention and of the disclosed types of dithiolopyrrolones, and their pharmacologically active and physiologically compatible derivatives, is useful for treating animals or humans that have, for example, leukemia, melanoma, cancers of the lung, colon, CNS, kidney, prostate, ovary, breast and the like using the accepted protocols of the National Cancer Institute (NCI). The dosage administered will be dependent upon the identity of the cancer or proliferative disease; the type of host involved including its age, health and weight; the kind of concurrent treatment, if any; and the frequency of treatment and therapeutic ratio. Illustratively, dosage levels of the administered active ingredients are intravenous, 0.1 to about 200 mg/kg; intramuscular, 1 to about 500 mg/kg; orally, 1 to about 1000 mg/kg; intranasal instillation, 1 to about 1000 mg/kg; and aerosol, 1 to about 1000 mg/kg of host body weight. Expressed in terms of concentration, an active ingredient can be present in the compositions of the present invention for localized use about the cutis, intranasally, pharyngolaryngeally, bronchially, bronchiolially, intravaginally, rectally, or ocularly in a concentration from about 0.01 to about 50% w/w of the composition; preferably about 1 to about 20% w/w of the composition; and for parenteral use in a concentration of from about 0.05 to about 50% w/v of the composition and preferably from about 5 to about 20% w/v. The disclosed specific compounds and types of dithiolopyrrolones, used as active ingredients to be employed as anticancer agents and antiproliferative agents, can be easily prepared in such unit dosage form with the employment of pharmaceutical materials which themselves are available in the art and can be prepared by established procedures.

In alternative aspects of the invention, the compounds of the invention may be used in treatments for cancers susceptible to such compounds, including both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas).

In some aspects of the invention, the types of dithiolopyrrolones and compounds of the invention are useful in treating proliferative diseases arising from hematopoietic malignancies such as leukemias (i.e. chloromas, plasmacytomas and the plaques and tumors of mycosis fungoides and cutaneous T-cell lymphomaileukemia) as well as in the treatment of lymphomas (both Hodgkin's and non-Hodgkin's lymphomas). In addition, the types of dithiolopyrrolone and compounds of the invention are useful in the prevention of metastases from the tumors described above either when used alone or in combination with radiotherapy and/or other chemotherapeutic agents.

In some aspects of the invention, the types of dithiolopyrrolone and the compounds of the invention are useful in treating other proliferative diseases such as blood vessel proliferative disorders, and fibrotic disorders such as cancers, tumors, hyperplasias, fibrosis (especially pulmonary fibrosis, but also other kinds of fibrosis, such as renal fibrosis), angiogenesis, psoriasis, atherosclerosis and smooth muscle cell proliferation in the blood vessels, such as stenosis or restenosis following angioplasty and skin proliferative diseases, such as psoriasis.

EXAMPLE 1

The antiproliferative activity of a particular dithiolopyrrolone can be demonstrated by standard assays. These assays are commonly used by those skilled in the art and are accepted as indicative of antiproliferative activity in mammals. The antiproliferative activities of the compounds of the invention have been determined in cell cultures of human ovarian cancer, using a standard anti-proliferative test of the US National Cancer Institute (NCI). [Monks, A. et al., *J. Natl. Cancer Inst.* 83(11): 757-766, 1991].

The compounds in this example are species of Formula I which show superior antiproliferative activity against proliferative ovarian cancer Ovcar-3 cell line (Table 1) in comparison with a dithiolopyrrolone, XN3 that was disclosed in U.S. Pat. No. 6,020,360 and WO 99012543 with anti-proliferative activities. The result showed that these novel dithiolopyrrolones have much stronger anti-proliferative activity than does XN3. The novel compound had activity against 56 cancer cell lines of a wide range of major cancers. (Table 1a).

Table 1a. Antiproliferative activity of novel compounds in comparison of XN3 against ovarian cancer cells, Ovar-3.

| Compounds | IC$_{50}$ (μM) |
|---|---|
| BLI-093 (BLI093) | 0.054 |
| 0037 (JS-02) | 0.071 |
| 0038 (JS-03) | 0.068 |
| 0058 (JS-38) | 0.034 |
| WBL-007 (WBI007) | 0.028 |
| WBL-018 | 0.070 |
| R3 (WBL-R3) | 0.078 |
| R4 (WBL-R4) | 0.046 |
| XN3 | 0.22 |

Table 1a. Anti-proliferative activity of the novel compound 0058 (JS-38) against 56 cancer cell lines.

| PROLIFERATIVE CELLS | IC$_{50}$(μM) |
|---|---|
| Leukemia | |
| CCRF-CEM | 0.01< |
| HL-60(TB) | 0.019 |
| K-562 | 0.019 |
| MOLT-4 | 0.15 |
| RPMI-8226 | 0.01< |
| SR | 0.02 |
| Non-Small Cell Lung Cancer | |
| A549/ATCC | 0.42 |
| EKVX | 0.13 |
| HOP-62 | 0.13 |
| HOP-92 | 0.18 |
| NCI-H226 | 0.27 |
| NCI-H23 | 0.21 |
| NCI-H322M | 8.56 |
| NCI-H460 | 0.26 |
| NCI-H522 | 0.19 |
| Colon Cancer | |
| COLO 205 | 0.15 |
| HCC-2998 | 0.11 |
| HCT-116 | 0.016 |
| HCT-15 | 0.02 |
| HT29 | 0.05 |
| KM12 | 2.97 |
| SW-620 | 0.034 |
| CNS Cancer | |
| SF-268 | 0.14 |
| SF-295 | 0.23 |
| SF-539 | 0.18 |
| SNB-19 | 0.23 |
| U251 | 0.15 |
| Melanoma | |
| LOX IMVI | 0.014 |
| MALME-3M | 0.19 |
| M14 | 0.24 |
| SK-MEL-2 | 0.18 |
| SK-MEL-28 | 0.016 |
| SK-MEL-5 | 0.12 |
| UACC-257 | 0.15 |
| UACC-62 | 0.19 |

| PROLIFERATIVE CELLS | IC$_{50}$(µM) |
|---|---|
| Ovarian Cancer | |
| IGROV1 | 0.17 |
| OVCAR-3 | 0.03 |
| OVCAR-5 | 0.45 |
| OVCAR-8 | 0.17 |
| Renal Cancer | |
| 786-0 | 0.06 |
| A498 | 0.19 |
| ACHN | 0.14 |
| CAKI-1 | 0.44 |
| RXF 393 | 0.04 |
| SN12C | 0.12 |
| TK-10 | 1.37 |
| UO-31 | 0.20 |
| Prostate Cancer | |
| PC-3 | 0.04 |
| DU-145 | 0.013 |
| Breast Cancer | |
| MCF7 | 0.17 |
| NCI/ADR-RES | 1.04 |
| MDA-MB-231/ATCC | 0.13 |
| HS 578T | 0.22 |
| MDA-MB-435 | 0.22 |
| BT-549 | 0.15 |
| T-47D | 0.013 |

EXAMPLE 2

Compounds shown in Table 2 were tested against cancer cell line H460 as set forth in Example 1, results showed that the ant-proliferative activity varied widely among derivatives with different modifications of the base dithiolopyrrolone structure.

Table 2. Anti-proliferative activity of compounds together with other dithiolopyrrolones against cancer cell lines H460 and LCC6.

| Compound | IC$_{50}$(µM) H460 |
|---|---|
| 0024 | 0.26 |
| 0066 | <0.01 |
| 0068 | <0.01 |
| 0069 | 0.04 |
| WBI-4 | <0.01 |
| WBI-5 | <0.01 |
| WBI-6 | 0.046 |
| 0136 | 0.092 |
| BLI-031-2 | >50 |
| 0044 | >1 |
| JS-26 | >1 |

EXAMPLE 3

The compounds of the present invention are prepared according to the following synthetic scheme (Scheme 1):

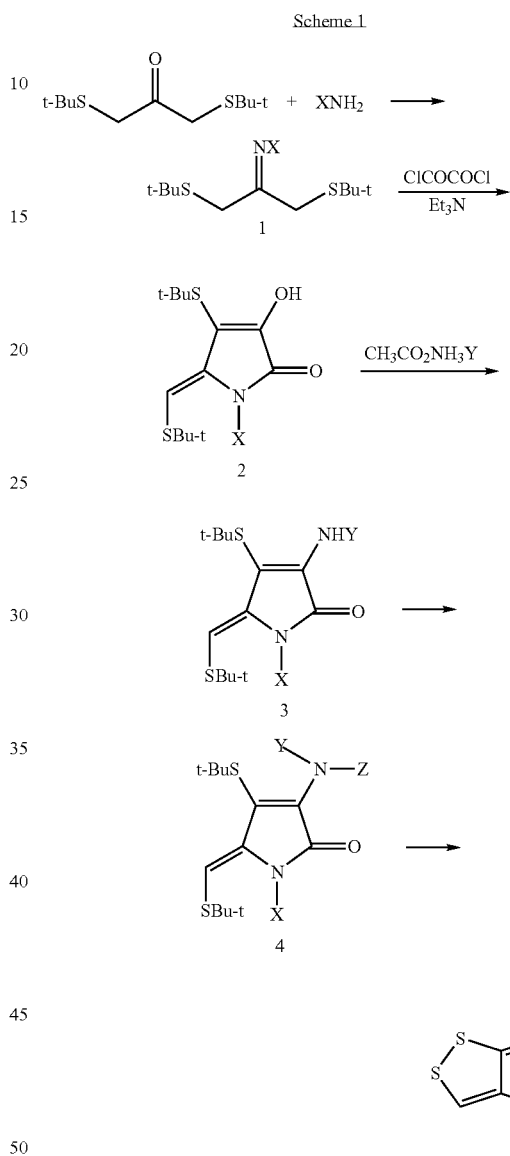

Intermediates prepared according to the above synthetic scheme (Scheme 1) procedure and used for the subsequent syntheses are listed in the following table.

| Intermediate | | X | Y | Z |
|---|---|---|---|---|
| 1 and 2 | a | 2,4-dimethoxyphenyl | | |
| | b | 1-ethylpyrazole-5-yl | | |
| | c | 3,4,5-trimethoxyphenyl | | |
| | d | benzyl | | |
| | e | phenyl | | |
| | f | 4-methylphenyl | | |
| | g | 4-methoxyphenyl | | |
| | h | 4-isobutylphenyl | | |

-continued

| Intermediate | | X | Y | Z |
|---|---|---|---|---|
| | i | 4-isopropanylphenyl | | |
| | j | methyl | | |
| 3 | a | 2,4-dimethoxyphenyl | H | |
| | b | 1-ethylpyrazole-5-yl | H | |
| | c | 3,4,5-trimethoxyphenyl | H | |
| | d | benzyl | H | |
| | e | phenyl | H | |
| | f | 4-methylphenyl | H | |
| | g | 4-methoxyphenyl | H | |
| | h | 4-isobutylphenyl | H | |
| | i | 4-isopropanylphenyl | H | |
| | j | methyl | H | |
| | k | H | H | |
| | l | 4-methoxyphenyl | benzyl- | |
| | m | 4-hydroxyphenyl | benzyl- | |
| | n | 2,4-dimethoxyphenyl | methyl | |
| 4 | a | 2,4-dimethoxyphenyl | H | acetyl |
| | b | 2,4-dimethoxyphenyl | H | nicotinoyl |
| | c | 2,4-dimethoxyphenyl | H | trifluoroacetyl |
| | d | 2,4-dimethoxyphenyl | methyl | methyl |
| | e | 2,4-dimethoxyphenyl | methylsulfonyl | methylsulfonyl |
| | f | 2,4-dimethoxyphenyl | 2-thiophenecarbonyl | 2-thiophenecarbonyl |
| | g | 2,4-dimethoxyphenyl | H | α-hydroxyacetyl |
| | h | H | H | nicotinoyl |
| | i | 4-methoxyphenyl | acetyl | acetyl |
| | j | 4-methoxyphenyl | H | trifluoroacetyl |
| | k | 4-methoxyphenyl | trifluoroacetyl | benzyl |
| | l | 4-hydroxyphenyl | trifluoroacetyl | benzyl |
| | m | 3,4,5-trimethoxyphenyl | H | acetyl |
| | n | 4-methylphenyl | H | acetyl |
| | o | 1-ethylpyrazole-5-yl | H | trifluoroacetyl |
| | p | 4-methyhoxyphenyl | H | acetyl |
| | q | 4-isobutylphenyl | H | trifluoroacetyl |
| | r | 4-isopropanylphenyl | H | trifluoroacetyl |
| | s | methyl | H | trifluoroacetyl |
| | t | benzyl | H | trifluoroacetyl |
| | u | 2,4-dimethoxyphenyl | methyl | trifluoroacetyl |

Detailed Synthesis:

Synthesis of compounds 1a-j. To a well stirred solution of 1,3-bis(t-butylthio)-acetone (10 mmol), $R^1NH_2$ (10 mmol) and triethylamine $Et_3N$ (20 mmol) in dry THF (100 ml), a solution of $TiCl_4$ (5.5 mmol) in 15 ml dry hexanes was added dropwise in 30 min at 0-5° C. under $N_2$. After the addition, the reaction mixture was refluxed for 2 hours. Imine compounds so obtained were used for the next step without purification of compound 1.

Synthesis of compounds 2a-j. At −10° C., oxalyl chloride (0.84 ml, 10 mmol) was added to the solution obtained in the previous step. At the same temperature and under stirring, $Et_3N$ (20 mmol) in 100 ml THF was added dropwise in 30 min. Then the solution was stirred at room temperature for 10 hours. The precipitate was filtered and washed with ether (250 ml). The organic solution was washed with water three times and the solvent was evaporated to give a dark brown power. It was recrystallized in ethyl acetate and hexanes to give a light yellow crystal of compound 2. All the compounds 2a-j can be prepared in the same way as described in these two steps. The total yield of these two steps for each of the compounds was about 60-70%.

Synthesis of compounds 3a-k. A 250 ml three neck flask with 50 g ammonium acetate was heated in oil bath under $N_2$ till $NH_4^+OAc^-$ melted. Compound 2 (5 mmol) was added into the flask and the resulting solution was stirred for one hour. The reaction temperature was within 140° C. to 165° C. depending on the proprieties of compound 2. One hour later, the heating was stopped and the reaction mixture was cooled to room temperature. The reaction mixture was dissolved in 100 ml water and extracted with 100 ml ether three times. The extracts were combined, dried over $Na_2SO_4$ and evaporated under reduced pressure. The residue was chromatographed on a column of silica gel to give compound 3. Yields for 3a-i were about 50-60%. Compound 3k was obtained as a by product in the preparations of compound 3a-j and it's yields depended on the reaction temperature and length of reaction time.

Synthesis of compounds 3l and 3m. A 150 ml flask with benzylamine acetate 30 g and Compound 2g (2 mmol) was heated to 170° C. under $N_2$. The mixture was stirred at this temperature for about one hour. When it was cooled, 50 ml water was added and it was extracted with 50 ml ether twice. The organic solvent was dried over $Na_2SO_4$ and evaporated under reduced pressure. The residue was purified with silica gel. Two compounds 3l and 3m were obtained with yields 25% and 15% respectively.

Synthesis of compounds 3n. A 100 ml flask with methylamine acetate 20 g and compound 2a (1 mmol) was heated to 170° C. under $N_2$. The mixture was stirred at this temperature for about one hour. When it was cooled, 50 ml water was added and it was extracted with 50 ml ether twice. The organic solvent was dried over $Na_2SO_4$ and evaporated under reduced pressure. The residue was purified with silica gel. 3n was obtained with yields of 40%.

Synthesis of 4a. To a well-stirred solution of 200 mg (0.474 mmol) of 3a in 10 ml of acetic anhydride, 20 mg of concentrated $H_2SO_4$ was added. Half a hour later, the solution was transferred on to a column of silica gel and developed with 200 ml $CH_2Cl_2$ then 500 ml of 20% ether in $CH_2Cl_2$ to give 4a 190 mg (0.41 mmol, 86%).

Synthesis of 4b. A solution of 3a 100 mg (0.24 mmol), nicotinoyl chloride hydrochloride 200 mg (1.12 mmol), and triethylamine 250 mg (2.47 mmol), in 10 ml THF was stirred for 24 hours at room temperature. Afterwards 50 ml of ether was added and the solution was washed with water three times. After it was dried over $Na_2SO_4$, the solvent was evaporated and the residue was purified on a column of silica gel to give 4b 90 mg (0.171 mmol, 72%).

Synthesis of 4c. To a solution of 3a 100 mg (0.24 mmol) in 5 ml of dichloromethane, 300 mg of trifluoroacetic anhydride was added. The resulting solution was stirred for half an hour and then the solvent was evaporated under reduced pressure to give 4c 122 mg (0.237 mmol, 100%).

Synthesis of 4d. In 5 ml of acetonitrile 211 mg 3a (0.5 mmol), 1 ml of formalin was mixed with 100 mg $NaCNBH_3$. While stirring, 0.1 ml glacial acetic acid was added dropwise over 30 minutes. This reaction mixture was stirred for 4 hours and another 0.1 ml glacial acetic acid was added in the middle of the course. It was diluted with 50 ml of ether and extracted with 1N NaOH, as well as with water. After it was dried and evaporated in a vacuum, the residue was chromatographed on a column of silica gel, 150 mg (0.33 mmol) of 4d was obtained in 67% yield.

Synthesis of 4e. To a solution of 3a 100 mg (0.24 mmol) and methylsulfonyl chloride 300 mg in 5 ml of dry THF, 300 mg of triethylamine was added drop by drop at room temperature in one minute. This solution was stirred for half an hour and 50 ml of ether was added and the solution was washed with water three times. After it was dried over $Na_2SO_4$, the solvent was evaporated and the residue was chromatographed on a column of silica gel to give 4e 110 mg (0.19 mmol, 80%).

Synthesis of 4f. A solution of 3a 100 mg (0.24 mmol), 2-thiophenecarbonyl chloride 200 mg (1.37 mmol) and trimethylamine 200 mg (1.98 mmol) in 10 ml of THF was refluxed for 10 hours. Afterwards 50 ml of ether was added and the solution was washed with water three times. After it was dried over $Na_2SO_4$, the solvent was evaporated and the residue was chromatographed on a column of silica gel to give 4f 120 mg (0.187 mmol, 79%).

Synthesis of 4g. A solution of 3a 100 mg (0.24 mmol), acetoxyacetyl chloride 118 mg (1.0 mmol) and triethylamine 120 mg (1.19 mmol), in 10 ml THF was stirred for 24 hours at room temperature. Afterwards 50 ml of ether was added and the solution was washed with water three times. The solvent was evaporated and the residue was dissolved in a solution of 0.1N sodium hydroxide 1 ml in methanol 10 ml. This solution was stirred for 1 hour. After the solvent was evaporated under reduced pressure, the residue was chromatographed on a column of silica gel to give 4g 105 mg (0.22 mmol, 91%).

Synthesis of 4h. A solution of 3j 100 mg (0.35 mmol), nicotinoyl chloride hydrochloride 250 mg (1.40 mmol), and triethylamine 350 mg (3.46 mmol), in 10 ml THF was stirred for 24 hours at room temperature. Afterwards 50 ml of ether was added and the solution was washed with water three times. After it was dried over $Na_2SO_4$, the solvent was evaporated and the residue was chromatographed on a column of silica gel to give 4h 100 mg (0.256 mmol, 73%).

Synthesis of 4i. A solution of 3g 100 mg (0.255 mmol), acetyl chloride 100 mg (1.28 mmol) and triethylamine 260 mg (2.56 mmol), in 10 ml_THF was stirred at 50° C. for 12 hours. Afterwards 50 ml of ether was added and the solution was washed with water three times. After it was dried over $Na_2SO_4$, the solvent was evaporated and the residue was chromatographed on a column of silica gel to give 4i 110 mg (0.231 mmol, 90%).

Synthesis of 4j. To a solution of 3g 100 mg (0.255 mmol) in 5 ml of dichloromethane, 300 mg of trifluoroacetic anhydride was added. The solution was stirred for half a hour and then the solvent was evaporated under reduced pressure to give 4j 125 mg (0.255 mmol, 100%).

Synthesis of 4k. To a solution of 3l 50 mg (0.104 mmol) in 5 ml of dichloromethane, 150 mg of trifluoroacetic anhydride was added. The solution was stirred for half an hour and then the solvent was evaporated under reduced pressure to give 4k 60 mg (0.104 mmol, 100%).

Synthesis of 4l. To a solution of 3m 50 mg (0.107 mmol) in 5 ml of dichloromethane, 200 mg of trifluoroacetic anhydride was added. The solution was stirred for half an hour and then the solvent was evaporated under reduced pressure to give 4l 60 mg (0.107 mmol, 100%).

Synthesis of 4m. A solution of 3c 100 mg (0.22 mmol), acetyl chloride 70 mg (0.9 mmol) and triethylamine 100 mg (0.99 mmol), in 10 ml THF was stirred at room temperature for 24 hours. Afterwards 50 ml of ether was added and the solution was washed with water three times. After it was dried over $Na_2SO_4$, the solvent was evaporated and the residue was chromatographed on a column of silica gel to give 4m 80 mg (0.162 mmol, 73%).

Synthesis of 4n. A solution of 3f 100 mg (0.266 mmol), acetyl chloride 70 mg (0.9 mmol) and triethylamine 100 mg (0.99 mmol), in 10 ml_THF was stirred at room temperature for 24 hours. Afterwards 50 ml of ether was added and the solution was washed with water three times. After it was dried over $Na_2SO_4$, the solvent was evaporated and the residue was chromatographed on a column of silica gel to give 4n 90 mg (0.215 mmol, 81%).

Synthesis of 4o. To a solution of 3b 80 mg (0.210 mmol) in 5 ml of dichloromethane, 300 mg of trifluoroacetic anhydride was added. The solution was stirred for half a hour and then the solvent was evaporated under reduced pressure to give 4o, 100 mg (0.210 mmol, 100%).

Synthesis of 4p. A solution of 3g 100 mg (0.255 mmol), acetyl chloride 50 mg (0.64 mmol) and triethylamine 1300 mg (1.28 mmol), in 10 ml_THF was stirred at 25° C. for 24 hours. Afterwards 50 ml of ether was added and the solution was washed with water three times. After it was dried over $Na_2SO_4$, the solvent was evaporated and the residue was chromatographed on a column of silica gel to give 4p 90 mg (0.19 mmol, 70%).

Synthesis of 4q. To a solution of 3h 100 mg (0.24 mmol) in 5 ml of dichloromethane, 300 mg of trifluoroacetic anhydride was added. The solution was stirred for half a hour and then the solvent was evaporated under reduced pressure to give 4q 120 mg (0.24 mmol, 100%).

Synthesis of 4r. To a solution of 3i 50 mg (0.124 mmol) in 5 ml of dichloromethane, 200 mg of trifluoroacetic anhydride was added. The solution was stirred for half an hour and then the solvent was evaporated under reduced pressure to give 4r 57 mg (0.124 mmol, 100%).

Synthesis of 4s. To a solution of 3j 50 mg in 5 ml of dichloromethane, 200 mg of trifluoroacetic anhydride was added. The solution was stirred for half an hour and then the solvent was evaporated under reduced pressure to give 4s 66 mg. Yield: 100%.

Synthesis of 4t. To a solution of 3d 50 mg in 5 ml of dichloromethane, 200 mg of trifluoroacetic anhydride was added. The solution was stirred for half an hour and then the solvent was evaporated under reduced pressure to give 4s 65 mg. Yield: 100%.

Synthesis of 4u. To a solution of 3n 50 mg in 5 ml of dichloromethane, 200 mg of trifluoroacetic anhydride was added. The solution was stirred for half an hour and then the solvent was evaporated under reduced pressure to give 4s 62 mg Yield: 100%.

Using these intermediates the compounds of the Table 3 are prepared.

TABLE 3

Novel dithiolopyrrolone derivatives.

| Code | X | Y | Z |
|---|---|---|---|
| BLI-017 | 4-Methoxyphenyl | H | Methyl |
| BLI-020 | 4-Methoxyphenyl | Acetyl | Methyl |
| BLI-023 | 4-Methoxyphenyl | H | Trifluoromethyl |
| BLI-031-2 | 2,4-Dimethoxy-phenyl | H | $CH_2CH_2COOH$ |
| BLI-038 | 4-Methylphenyl | H | Methyl |
| BLI-044 | 4-Methoxyphenyl | Benzyl | Trifluoromethyl |
| BLI-045 | 4-Hydroxyphenyl | Benzyl | Trifluoromethyl |
| BLI-053 | 2,4-Dimethoxy-phenyl | H | Methyl |
| BLI-063 | 3,4,5-trimethoxy-phenyl | H | Methyl |
| BLI-065 | 2,4-Dimethoxy-phenyl | H | 3-pyridyl |
| BLI-066 | 2,4-Dimethoxy-phenyl | H | N-methyl-3-pyridinium chloride |
| BLI-075 | 2,4-Dimethoxy-phenyl | H | Trifluoromethyl |
| BLI-079 | 1-ethylpyrazole-5-yl | H | Trifluoromethyl |
| BLI-081 | 2,4-Dimethoxy-phenyl | H | 2-furyl |
| BLI-090 | 2,4-Dimethoxy-phenyl | H | 2,4-dimethoxyphenyl |
| BLI-093 | 2,4-Dimethoxy-phenyl | H | 4-Trifluoromethylphenyl |
| WBL-004 | 2,4-Dimethoxy-phenyl | 2-thio-phenylcarboxy | 2-thiophenyl |
| WBL-007 | 2,4-Dimethoxy-phenyl | H | 2-thiophenyl |
| R1 | 2,4-Dimethoxy-phenyl | H | Hydroxymethyl |
| R2 | 2,4-Dimethoxy-phenyl | H | hexyl |
| R3 | 2,4-Dimethoxy-phenyl | H | 3,5-difluorophenyl |
| R4 | 2,4-Dimethoxy-phenyl | H | 2,3,4-trifluorophenyl |
| WBL-018 | 2,4-Dimethoxy-phenyl | H | 4-fluoro-phenyl |
| 0037 | 2,4-Dimethoxy-phenyl | H | Thiophene-2-methyl |
| 0038 | 2,4-Dimethoxy-phenyl | H | 4-nitrophenyl |
| 0039 | 2,4-Dihydroxyphenyl | H | methyl |
| 0040 | 2,4-Dimethoxy-phenyl | H | 4-N,N-dimethylamine-phenyl |
| 0041 | 2,4-Dimethoxy-phenyl | H | 4-aminophenyl |
| 0042 | 2,4-Dimethoxy-phenyl | H | 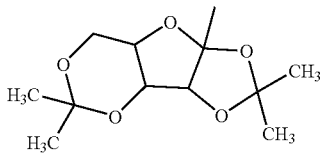 |
| 0043 | 2,4-Dimethoxy-phenyl | H | 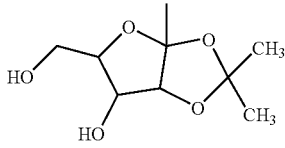 |
| 0044 | 2,4-Dimethoxy-phenyl | H | 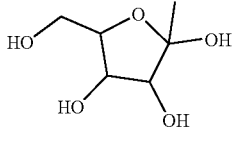 |
| 0047 | 2,4-Dimethoxy-phenyl | H | 3-trifluoromethylphenyl |
| 0052 | 2,4-Dimethoxy-phenyl | H | 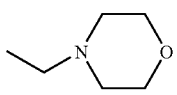 |
| JS-26 | 2,4-Dimethoxy-phenyl | H | 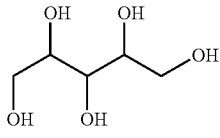 |
| 0054 | 4-iso-butylphenyl | H | 4-trifluoromethylphenyl |
| 0055 | 4-iso-butylphenyl | H | 2-furyl |
| 0056 | 4-iso-butylphenyl | H | 2-thiophenyl |
| 0057 | 4-iso-butylphenyl | H | 3-trifluoromethylphenyl |
| 0058 | 2,4-Dimethoxy-phenyl | H | 3,5-di-trifluoromethylphenyl |

TABLE 3-continued

Novel dithiolopyrrolone derivatives.

| Code | X | Y | Z |
|---|---|---|---|
| 0059 | 4-iso-butylphenyl | H | 3,5-di-trifluoromethylphenyl |
| 0062 | 2,4-Dimethoxy-phenyl | H | 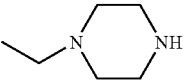 |
| 0066 | 2,4-Dimethoxy-phenyl | H | 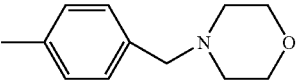 |
| 0068 | 2,4-Dimethoxy-phenyl | H | 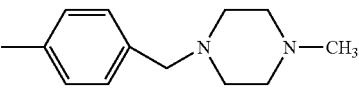 |
| 0069 | 2,4-Dimethoxy-phenyl | H | 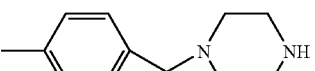 |
| WBI-4 | 4-isopropylphenyl | H | 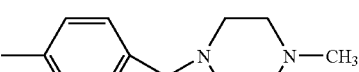 |
| WBI-5 | 4-isobutylphenyl | H | 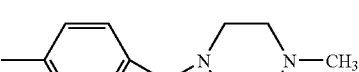 |
| WBI-6 | methyl | H | 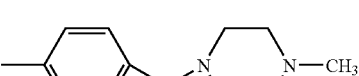 |
| 0096 | 4-isopropanylphenyl | H | 3,5-dihydroxy-4-isopropanyl-phenyl |
| 0102 | 2,4-Dimethoxy-phenyl | H | 3,5-dihydroxy-4-isopropanyl-phenyl |
| 0107 | Benzyl | H | 3,5-dihydroxy-4-isopropanyl-phenyl |
| 0110 | methyl | H | 3,5-dihydroxy-4-isopropanyl-phenyl |
| 0113 | Benzyl | H | 2-thiophenyl |
| 0116 | Benzyl | H | 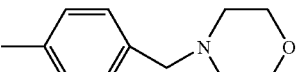 |
| 0122 | 2,4-Dimethoxy-phenyl | methyl |  |
| 0125 | 4-isopropanylphenyl | H | 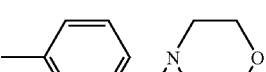 |
| 0126 | 2,4-Dimethoxy-phenyl | H | 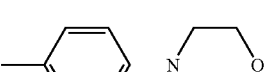 |
| 0128 | 4-isopropanylphenyl | H | Pyridine-3-yl |
| 0135 | Benzyl | H | Pyridine-3-yl |
| 0136 | Benzyl | H | 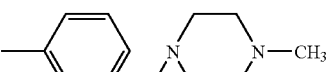 |
| 0137 | Benzyl | H | 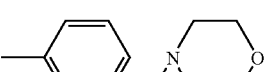 |
| CSL-25 | Phenyl | H | Methyl |

TABLE 3-continued

Novel dithiolopyrrolone derivatives.

| Code | X | Y | Z |
|---|---|---|---|
| CSL-26 | Benzyl | H | Phenyl |
| CSL-28 | H | H | 3-pyridyl |
| | 2,4-Dimethoxy-phenyl | H | 2-(2-thiophenyl)-vinyl |
| | 2,4-Dimethoxy-phenyl | H | 1-methylimidazol-5-yl |
| | 4-Methyl-phenyl | H | 2-thiophenyl |
| | H | H | 2-thiophenyl |
| | H | Methyl | 2-thiophenyl |
| | 2,4-Dimethoxy-phenyl | Methyl | 2-thiophenyl |
| | 2,4-Dimethoxy-phenyl | benzyl | 2-furyl |
| | 2,4-Dimethoxy-phenyl | H | 1-methyl- pyrrolyl |
| | cyclohexyl | H | phenyl |
| | benzyl | H | phenyl |
| | H | cyclohexyl | phenyl |
| | H | 2-thiazolyl | phenyl |
| | 2,4-dimethoxy-phenyl | H | 2-thiazolyl |
| | 2,4-Dimethoxy-phenyl | H | propyl |
| | 2,4-Dimethoxy-phenyl | H | N-methy-2-lindolyl |

Synthesis of BLI-017. A solution of 4p 90 mg (0.19 mmol) and Hg (OAc)$_2$ 6.8 mg (0.19 mmol) in 10 ml TFA was stirred at room temperature for one hour. After TFA was evaporated under reduced pressure, the residue was dissolved in 100 ml CH$_3$CN. H$_2$S was bubbled into the solution. One hour later, N$_2$ was bubbled into the solution to drive away trace of H$_2$S, then 0.20 mmol I$_2$ in 10 ml CH$_2$Cl$_2$ was added to the solution. Half an hour later, the solvent was evaporated under reduced pressure and the residue was chromatographed in a column of silica gel to give BLI-017 43 mg. Yield 67%. $^1$H NMR(100 MHz, CDCl$_3$) δ 2.2(s, 3H), 3.9(s, 3H), 6.7(s, 1H), 7.0-7.4(dd, 4H), 7.8(s, 1H).

Synthesis of BLI-020. BLI-020 was synthesized from 4i by the same method of synthesis as BLI-017. Yield: 60%. $^1$H NMR(100 MHz, CDCl$_3$) δ 2.5(s, 6H), 3.9(s, 3H), 6.95(s, 1H), 7.0-7.5(dd, 4H), MS(CI): 363(M+1).

Synthesis of BLI-023. BLI-023 was synthesized from 4j by the same method of synthesis as BLI-017. Yield 75%. $^1$H NMR(100 MHz, CDCl$_3$) δ 3.9(s, 3H), 6.82(s, 1H), 7.0-7.4 (dd, 4H), 8.3(s, 1H).

Synthesis of BLI-038. BLI-038 was synthesized from 4n by the same method of synthesis as BLI-017. yield: 70% $^1$H NMR(100 MHz, CDCl$_3$) δ 2.1(s, 3H), 2.4(s, 3H), 6.7(s, 1H), 7.3(s, 4H), 8.0(s, 1H).

Synthesis of BLI-044. BLI-044 was synthesized from 4k by the same method of synthesis as BLI-017. Yield: 72%. $^1$H NMR (100 MHz, CDCl$_3$) δ 3.9(s, 3H), 4.2-5.8(dd, 2H), 6.9(s, 1H), 7.0-7.4(dd, 4H), 7.4(s, 5H). MS(CI): 465(M+1).

Synthesis of BLI-045. BLI-045 was synthesized from 4l by the same method of synthesis as BLI-017. Yield: 65%. $^1$H NMR(100 MHz, CDCl$_3$) δ 4.2-5.8(dd, 2H), 6.6(s, 1H), 7.1-7.5(broad peak, 9H), 7.4(s, 5H).

Synthesis of BLI-053. BLI-053 was synthesized from 4 by the same method of synthesis as BLI-017. Yield: 77%. $^1$H NMR (100 MHz, CDCl$_3$) δ 3.77(s, 3H), 3.82(s, 3H), 6.6(s, 1H), 6.4-7.3(multi, 3H), 8.0(broad peak, 1H). MS: 350(M).

Synthesis of BLI-063. BLI-063 was synthesized from 4m by the same method of synthesis as BLI-017. Yield: 55%. $^1$H NMR(100 MHz, CDCl$_3$) δ 3.8(s, 6H), 3.9(s, 3H), 6.7(s, 1H), 7.4(s, 2H), 7.9(broad peak, 1H). MS: 380(M).

Synthesis of BLI-065. BLI-065 was synthesized from 4b by the same method of synthesis as BLI-017. Yield: 45%. $^1$H NMR(100 MHz, CD$_3$OD) δ 3.8(s,3H), 3.9(s, 3H), 6.7(s, 1H), 6.6-9.2(multi, 7H).

Synthesis of BLI-066. 10 mg (0.024 mmol) BLI-065 was dissolved in 1 ml CH$_3$I and the solution left at room temperature for 10 hours. Red crystals formed in the solution which was filtered and 9 mg (0.016 mmol) BLI-066 was obtained in 67%. $^1$H NMR(100 MHz, CD$_3$OD) δ 3.7(s, 3H), 3.8(s, 3H), 4.4(s, 3H), 6.9(s, 1H), 6.5-9.4(multi, 7H).

Synthesis of BLI-075. BLI-075 was synthesized from 4c by the same method of synthesis as BLI-017. Yield: 83%. $^1$H NMR(100 MHz, CDCl$_3$) δ 3.8(s, 3H), 3.9(s, 3H), 6.6(multi, 3H), 7.2(d, 1H), 8.4(s, 1H). MS: CI 405(M+1).

Synthesis of BLI-079. BLI-079 was synthesized from 4o by the same method of synthesis as BLI-017. Yield: 6.6%. $^1$H NMR(100 MHz, CDCl$_3$) δ 1.5(t, 3H), 4.0(q, 2H), 6.3(d, 1H), 6.9(s, 1H), 7.7(d, 1H), 8.4(s, 1H). MS: CI 363(M+1).

Synthesis of 0024. 0024 was synthesized from 4d by the same method of synthesis as BLI-017.19%. $^1$H NMR(100 MHz, CDCl$_3$) δ 2.6(s, 6H), 3.8(s, 3H), 3.9(s, 3H), 6.4(s, 1H), 6.5(multi, 2H), 7.2(d, 1H). MS: 337(M+1).

Synthesis of WBL-004. WBL-004 was synthesized from 4f by the same method of synthesis as BLI-017. Yield: 43%. $^1$H NMR (100 MHz, CDCl$_3$), δ 3.8(s, 3H), 3.9(s, 3H), 6.5(s, 1H), 6.65(multi, 4H), 7.2(multi, 2H), 7.7(multi, 3H). MS: 529(M+1).

Synthesis of R1. R1 was synthesized from 4g by the same method of synthesis as BLI-017. Yield: 41%. $^1$H NMR (100 MHz, CDCl$_3$), δ 3.8(s, 3H), 3.9(s, 3H), 4.3(s, 2H), 6.5(s, 1H), 6.65(multi, 2H), 7.2(d, 1H), 8.35(s, 1H). MS: 367(M+1).

Synthesis of CSL-25. CSL-25 was synthesized using the procedure of Scheme 1. CSL-25 has the following characteristics: $^1$H NMR (100 MHz, CDCl$_3$) δ 2.2(s, 3H), 6.8(s, 1H), 7.4-7.6(multi, 5H), 7.8(s, 1H).

Synthesis of CSL-26. CSL-26 was synthesized using the procedure of Scheme 1. CSL-26 has the following characteristics: $^1$H NMR (100 MHz, CDCl$_3$) δ 5.1(s, 2H), 6.5(s, 1H), 7.2-8.0(multi, 10H), 8.3(s, 1H).

Synthesis of CSL-28. CSL-28 was synthesized from 4h by the same method of synthesis as BLI-017. Yield: 43%. $^1$H NMR (100 MHz, CDCl$_3$), δ 6.8(s, 1H), 7.9(s, 1H), 8.1-9.2 (multi 4H), MS: CI, 278(M+1).

Synthesis of 0050. 0050 was synthesized from 4q by the same method of synthesis as BLI-017. Yield: 80%. $^1$H NMR (100 MHz, CDCl$_3$), δ 0.9(t, 3H), 1.3(d, 3H), 1.65(multi, 2H), 2.7(multi, 1H), 6.9(s, 1H), 7.3(s, 4H), 8.4(s, 1H).

Synthesis of 0061. 0061 was synthesized from 4s by the same method of synthesis as BLI-017. Yield: 82%. $^1$H NMR (100 MHz, CDCl$_3$), 2.8(s, 3H), 6.6(s, 1H), 8.4(s, 1H).

Synthesis of 0092. 0092 was synthesized from 4r by the same method of synthesis as BLI-017. Yield: 77%. ¹H NMR (100 MHz, CDCl₃), δ 1.26(d, 6H), 3.0(multi, 1H), 6.7(s, 1H), 7.35(s, 4H), 8.6(s, 1H).

Synthesis of 0103. 0103 was synthesized from 4t by the same method of synthesis as BLI-017. Yield: 85%. ¹H NMR (100 MHz, CDCl₃), 4.3(s, 2H), 6.6(s, 1H), 7.3(s, 5H), 8.4(s, 1H).

Synthesis of 0119. 0119 was synthesized from 4u by the same method of synthesis as BLI-017. Yield: 85%. ¹H NMR (100 MHz, CDCl₃), δ 2.7(s, 3H), 3.8(s, 3H), 3.85(s, 3H),), 6.55(s, 1H), 6.6(multi, 2H),), 7.2(d, 1H), 8.4(s, 1H).

EXAMPLE 4

The following compounds of the Examples 1-3 are prepared according to the following synthetic scheme (Scheme 2):

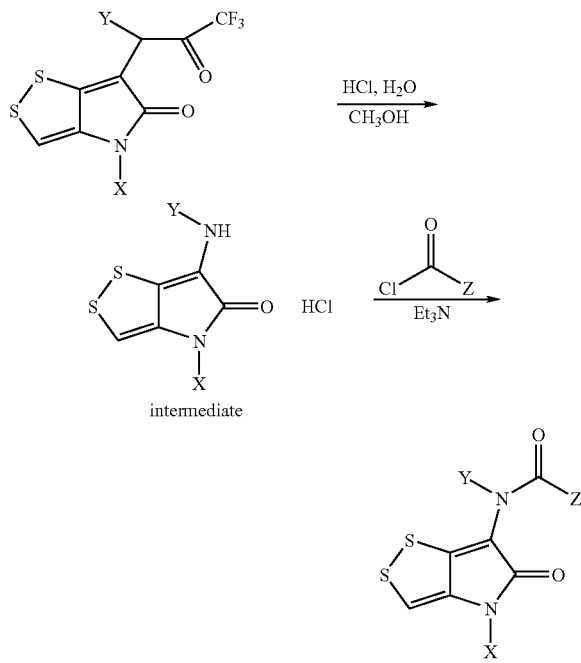

According to this scheme the following intermediates are synthesized

| Code | X | Y |
|---|---|---|
| 0021 | 2,4-dimethoxyphenyl | H |
| 0051 | 4-isobutylphenyl | H |
| 0079 | Methyl | H |
| 0093 | 4-isopropanylphenyl | H |
| 0104 | Benzyl | H |
| 0120 | 2,4-dimethoxyphenyl | Methyl |

Detailed Synthesis:

Synthesis of 0021. 1 g BLI-075 was dissolved in a solution of 5 ml hydrochloric acid in 150 ml methanol. The solution was refluxed for 2 hours. After the solvent was evaporated in vacuum, 0.76 g 0021 was collected as a dark green powder.

Synthesis of BLI-081. 50 mg (0.16 mmol) 0021 was dissolved in 20 ml dry THF. While thoroughly stirring, 43 mg (0.32 mmol) 2-furoyl chloride was added first then 50 mg triethylamine was added dropwise over 2 minutes. The reaction was completed in half an hour and the product was purified by a column of silica gel to give 51 mg (0.12 mmol, 80%) BLI-081. ¹H NMR(100 MHz, CDCl₃) δ 3.8(s, 3H), 3.9(s, 3H), 6.5(s, 1H), 6.6(s multi, 3H), 7.2(multi, 2H), 7.6(d, 1H), 8.4(s, 1H). MS: 403(M+1).

Synthesis of BLI-090. BLI-090 was synthesized by the reaction of 0021 with 2,4-dimethoxy benzoyl chloride by the same method of synthesis as BLI-081. Yield: 89%. ¹H NMR (100 MHz, CDCl₃) δ 3.8(s, 3H), 3.9(s, 3H), 3.93(s, 3H), 4.07(s, 3H), 6.4(s, 1H), 6.6(multi, 4H), 7.2(d, 1H), 8.2(d, 1H), 10.2(s, 1H). MS: 473(M+1).

Synthesis of BLI-093. BLI-093 was synthesized by the reaction of 0021 with 4-trifluoromethyl benzoyl chloride by the same method of synthesis as BLI-081. Yield: 90%. ¹H NMR(100 MHz, CDCl₃) δ 3.8(s, 3H), 3.9(s, 3H), 6.5(s, 1H), 6.6(multi, 2H), 7.25(d, 1H), 7.8(d, 2H), 8.1(d, 2H), 8.4(s, 1H). MS: 480(M).

Synthesis of WBL-007. WBL-007 was synthesized by the reaction of 0021 with 2-thiophenecarbonyl chloride by the same method of synthesis as BLI-081. Yield: 88%. ¹H NMR (100 MHz, CDCl₃), δ 3.8(s, 3H), 3.9(s, 3H), 6.55(s, 1H), 6.63(multi, 2H), 7.2(multi, 2H), 7.7(multi, 2H). MS: 418(M).

Synthesis of R2. R2 was synthesized by the reaction of 0021 with heptanoyl chloride by the same method of synthesis as BLI-081. Yield: 74%. ¹H NMR (100 MHz, CDCl₃), δ 0.9 (t, 3H), 1.4(multi, 8H), 2.4(t, 2H), 3.8(s, 3H), 3.9(s, 3H), 4.3(s, 2H), 6.6(s, 1H), 6.65(multi, 2H), 7.2(d, 1H), 8.4(s, 1H). MS: 420(M).

Synthesis of R3. R3 was synthesized by the reaction of 0021 with 3,4-difluorobenzoyl chloride by the same method of synthesis as BLI-081. Yield: 81%. ¹H NMR (100 MHz, CDCl₃), δ 3.8(s, 3H), 3.9(s, 3H), 6.5(s, 1H), 6.6 (multi, 2H), 7.1 (multi, 2H), 7.5(multi, 2H), 8.4(s, 1H). MS: 448(M).

Synthesis of R4. R4 was synthesized by the reaction of 0021 with 2,3,4-trifluorobenzoyl chloride by the same method of synthesis as BLI-081. Yield: 84%. ¹H NMR (100 MHz, CDCl₃), δ 3.8(s, 3H), 3.9(s, 3H), 6.5(s, 1H), 6.6 (multi, 2H), 7.2 (multi, 2H), 7.9(multi, 1H), 8.6(s, 1H). MS: 466(M).

Synthesis of WBL-018. WBL-018 was synthesized by the reaction of 0021 with 4-fluorobenzoyl chloride by the same method of synthesis as BLI-081. Yield: 85%. ¹H NMR (100 MHz, CDCl₃), δ 3.8(s, 3H), 3.9(s, 3H), 6.5(s, 1H), 6.65(multi, 3H), 7.1 (multi, 2H), 7.5(multi, 2H), 8.4(s, 1H). MS: 430(M).

Synthesis of 0037. 0037 was synthesized by the reaction of 0021 with thiopheneacetyl chloride by the same method of synthesis as BLI-081. Yield: 81%. ¹H NMR (100 MHz, CDCl₃), δ 3.75(s, 3H), 3.85(s, 3H), 3.9(s, 2H), 6.42(s, 1H), 6.55(multi, 2H), 7.1-7.3 (multi, 4H), 8.2(s, 1H).

Synthesis of 0038. 0038 was synthesized by the reaction of 0021 with 4-nitrobenzoyl chloride by the same method of synthesis as BLI-081. Yield: 81%. ¹H NMR (100 MHz, CDCl₃), δ 3.8(s, 3H), 3.85(s, 3H), 6.55(multi, 3H), 7.1-7.3 (dd, 1H), 8.2(dd, 4H), 8.9(s, 1H).

Synthesis of 0040. 100 mg (0.32 mmol), 0021 55 mg (0.32 mmol) 4-(dimethylamino)benzoic acid and 75 mg (0.34 mmol) DCC were dissolved in 20 ml dry CH₂Cl₂. This solution had been stirred for 2 hours. After the solvent was evaporated, product was purified by a column of silica gel to give 65 mg (60%) 0040. ¹H NMR (100 MHz, CDCl₃), δ 3.1(s, 6H), 3.8(s, 3H), 3.85(s, 3H), 6.4(s, 1H), 6.5(multi, 2H), 6.8(d, 2H), 7.25(d, 1H), 7.85(d, 2H), 8.1(s, 1H).

Synthesis of 0041. 100 mg (0.32 mmol), 0021 80 mg (0.32 mmol) 4-trifloroacetamidobenzoic acid and 75 mg (0.34 mmol) DCC were dissolved in 20 ml dry CH₂Cl₂. This solution had been stirred for 2 hours. After the solvent was evaporated, residue was dissolved in 40 ml methanol. To this solution 2 ml concentrated HCl was added and the resulting solution was refluxed for 1 hour. Product was extracted with ethyl acetate and washed with water dried on sodium sulfate. After solvent was evaporated the residue was chromatographed on a column of silica gel to give 50 mg (40%) 0041. $^1$H NMR (100 MHz, DMSO-$d_6$), δ 3.7(s, 3H), 3.8(s, 3H), 5.9(s, 2H), 6.6(d, 2H), 6.7 (multi, 2H), 6.8(s, 1H), 7.2(d, 1H), 7.75(d, 2H), 9.55(s, 1H).

Synthesis of 0042. 100 mg (0.32 mmol), 0021, 100 mg (0.33 mmol) 2,3:4,6-di-O-isopropylidene-2-keto-L-gulonic acid monohydrate and 80 mg (0.35 mmol) DCC were dissolved in 20 ml dry $CH_2Cl_2$. This solution had been stirred for 2 hours. After the solvent was evaporated, residue was chromatographed on a column of silica gel to give 110 mg (60%) 0042. $^1$H NMR (100 MHz, $CDCl_3$), δ 1.4(s, 3H), 1.42(s, 3H), 1.6(s, 6H), 3.75(s, 3H), 3.85(s, 3H), 4.1-4.7(multi, 5H), 6.4(s, 1H), 6.5-6.6(multi, 2H), 7.2(d, 1H), 9.0(s, 1H).

Synthesis of 0043. A solution of 50 mg 0042 in 20 ml mixture of 1N HCl and THF (1:5) was stirred at room temperature for 3 hours. Product was extracted with ethyl acetate and washed with water. After solvent was evaporated, residue was chromatographed on a column of silica gel to give 42 mg (85%) 0043. $^1$H NMR (100 MHz, $CDCl_3$), δ 1.4(s, 3H), 1.42(s, 3H), 3.8(s, 3H), 3.9(s, 3H), 4.1-4.7(multi, 5H), 6.5(s, 1H), 6.5-6.6(multi, 2H), 7.2(d, 1H), 9.0(s, 1H).

Synthesis of 0044. A solution of 50 mg 0042 in 20 ml mixture of acetic acid and water (7:3) was refluxed for 4 hours. Solvents were evaporated under reduced pressure. Residue was chromatographed on a column of silica gel to give 36 mg (85%) 0044. $^1$H NMR(100 MHz, $CDCl_3$), δ 2.6-4.5(broad, 10H), 3.8(s, 3H), 3.9(s, 3H), 6.5-6.6(multi, 3H), 7.2(d, 1H), 9.0(s, 1H).

Synthesis of 0047. The synthesis of 0047 was achieved by the reaction of 0021 with 3-trifluoromethylbenzoyl chloride by the same method of synthesis as BLI-081. Yield: 85%. $^1$H NMR (100 MHz, $CDCl_3$), δ 3.8(s, 3H), 3.85(s, 3H),), 6.55(s, 1H), 6.6(multi, 2H), 7.2(d, 1H), 7.8(s, 1H), 7.7-8.4(multi, 4H).

Synthesis of 0051. The synthesis of 0051 was achieved form 0050 by the same method of synthesis as 0021. Yield: 90%.

Synthesis of 0052. 100 mg 0021 was dissolved in 40 ml dry THF. While stirring thoroughly, 100 mg chloroacetyl chloride was added then 50 mg triethylamine was added dropwise over 2 minutes. The reaction was completed in half an hour. Product was extracted with ethyl acetate and washed with water. After the solvent was evaporated the residue was dissolved in 10 ml of acetonitrile. To this solution, 0.5 ml of morpholine was added and the solution was stirred at 60° C. for 4 hours. Product was extracted with ethyl acetate and washed with water. After solvent was evaporated, residue was chromatographed on a column of silica gel to give 0052 65 mg Yield: 50%. $^1$H NMR (100 MHz, $CDCl_3$), δ 2.8(multi, 4H), 3.8 (multi, 4H), 3.81(s, 3H), 3.85(s<3H), 6.45(s, 1H), 6.6(multi, 2H), 7.25(d, 1H), 9.45(s, 1H).

Synthesis of 0054. The compound 0054 was synthesized by the reaction of 0051 and 4-trifluromethyl benzoyl chloride using the same method of synthesis as for BLI-081. Yield: 85%. $^1$H NMR (100 MHz, $CDCl_3$), δ 0.9(t, 3H), 1.3(d, 3H), 1.65(multi, 2H), 2.7(multi, 1H), 6.9(s, 1H), 7.3(s, 4H), 7.8(d, 2H), 8.1(d, 2H), 8.4(s, 1H).

Synthesis of 0055. The compound 0055 was synthesized by the reaction of 0051 and 2-furoyl chloride using the same method of synthesis as for BLI-081. Yield: 90%. $^1$H NMR (100 MHz, $CDCl_3$), δ 0.9(t, 3H), 1.3(d, 3H), 1.65(multi, 2H), 2.7(multi, 1H), 6.6(dd, 1H), 6.9(s, 1H), 7.3(s, 4H), 7.4(d, 1H), 7.6(d, 1H), 8.4(s, 1H).

Synthesis of 0056. The compound 0056 was synthesized by the reaction of 0051 and 2-thiophenecarbonyl chloride using the same method of synthesis as for BLI-081. Yield: 90%. $^1$H NMR (100 MHz, $CDCl_3$), δ 0.9(t, 3H), 1.3(d, 3H), 1.65(multi, 2H), 2.7(multi, 1H), 6.85(s, 1H), 7.2(dd, 1H), 7.3(s, 4H), 7.6(d, 2H), 7.8(d, 2H), 8.2(s, 1H).

Synthesis of 0057. The compound 0057 was synthesized by the reaction of 0051 and 3-trifloromethyl benzoyl chloride using the same method of synthesis as for BLI-081. Yield: 88%. $^1$H NMR (100 MHz, $CDCl_3$), δ 0.9(t, 3H), 1.3(d, 3H), 1.65(multi, 2H), 2.7(multi, 1H), 6.9(s, 1H), 7.35(s, 4H), 7.6-8.3(multi, 4H), 8.4(s, 1H).

Synthesis of 0058. The compound 0058 was synthesized by the reaction of 0021 and 3,5-di-trifloromethyl benzoyl chloride using the same method of synthesis as for BLI-081. Yield: 88%. $^1$H NMR (100 MHz, $CDCl_3$), δ 3.8(s, 3H), 3.85 (s, 3H),), 6.55(s, 1H), 6.6(multi, 2H),), 7.2(d, 1H), 8.1(s, 1H), 8.4(s, 2H), 8.6(s, 1H).

Synthesis of 0059. The compound 0059 was synthesized by the reaction of 0051 and 3,5-di-trifloromethyl benzoyl chloride using the same method of synthesis as for BLI-081. Yield: 80%. $^1$H NMR (100 MHz, $CDCl_3$), δ 0.9 (t, 3H), 1.3(d, 3H), 1.65(multi, 2H), 2.7(multi, 1H), 6.95(s, 1H), 7.3(s, 4H),), 8.1(s, 1H), 8.4(s, 2H), 8.6(s, 1H).

Synthesis of 0062. 100 mg 0021 was dissolved in 40 ml dry THF. While stirring thoroughly, 100 mg chloroacetyl chloride was added, then 100 mg triethylamine was added dropwise over 2 minutes. The reaction was completed in half an hour. Product was extracted with ethyl acetate and washed with water. After the solvent was evaporated the residue was dissolved in 10 ml of DMF. To this solution, 200 mg of piperazine was added and the solution was stirred at 60° C. for 4 hours. Product was extracted with ethyl acetate and washed with water. After solvent was evaporated, the residue was chromatographed on a column of silica gel to give 0062 70 mg Yield: 53%. $^1$H NMR (100 MHz, $CDCl_3$), δ 2.7(multi, 4H), 3.1(multi, 4H), 3.2(s, 2H), 3.4(s, 1H), 3.8(s, 3H), 3.9(s, 3H), 6.4(s, 1H), 6.6(multi, 2H), 7.2(d, 1H), 9.2(s, 1H).

Synthesis of 0066. 100 mg 0021 was dissolved in 40 ml dry THF. While stirring thoroughly, 120 mg 4-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of morpholine. This solution was stirred at 60° C. for 2 hours and water was added. Product was extracted with ethyl acetate and washed with water. After solvent was evaporated, the residue was chromatographed on a column of silica gel to give 0066 110 mg. Yield: 68%. $^1$H NMR (100 MHz, $CDCl_3$), δ 2.5 (multi, 4H), 3.8(multi, 4H), 3.6(s, 2H), 3.85(s, 3H), 3.9(s, 3H), 6.5(s, 1H), 6.6(multi, 2H), 7.2(d, 1H), 7.7(dd, 4H), 8.3(s, 1H).

Synthesis of 0068. 100 mg 0021 was dissolved in 40 ml dry THF. While stirring thoroughly, 120 mg 4-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of N-methyl piperazine. This solution was stirred at 60° C. for 2 hours and water was added. Product was extracted with ethyl acetate and washed with water. After solvent was evaporated, the residue was chromatographed on a column of silica gel to give 0068 120 mg Yield: 70%. $^1$H NMR (100 MHz, $CDCl_3$), δ 2.4(s, 3H), 2.6(s, 8H), 3.6(s, 2H), 3.85(s, 3H), 3.9(s, 3H), 6.45(s, 1H), 6.6(multi, 2H), 7.2(d, 1H), 7.7(dd, 4H), 8.3(s, 1H).

Synthesis of 0069. 100 mg 0021 was dissolved in 40 ml dry THF. While stirring thoroughly, 120 mg 4-chloromethyl benzonyl chloride was added, then 100 mg triethylamine was added dropwise over 2 minutes. The reaction was completed in half an hour. Product was extracted with ethyl acetate and washed with water. After the solvent was evaporated the residue was dissolved in 10 ml of DMF. To this solution, 200 mg of piperazine was added and the solution was stirred at 60° C. for 4 hours. Product was extracted with ethyl acetate and washed with water. After the solvent was evaporated, the residue was chromatographed on a column of silica gel to give 0069 125 mg Yield: 70%. $^1$H NMR (100 MHz, $CDCl_3$), δ 2.6(s, 4H), 3.1(multi, 4H), 3.6(s, 2H), 3.85(s, 3H), 3.9(s, 3H), 6.5(s, 1H), 6.6(multi, 2H), 7.25(d, 1H), 7.7(dd, 4H), 8.4(s, 1H).

Synthesis of 0079. The compound 0079 was synthesized from 0061 by the same method as the synthesis of 0021. It is a dark green powder.

Synthesis of 0080. 80 mg 0079 was dissolved in 20 ml of dry THF. To this solution 150 mg of 3-nicotinoyl carbonyl chloride was added and 100 mg of triethylamine was added dropwise. The resulting solution was stirred at room temperature for half an hour. Product was extracted with ethyl acetate and washed with water. After solvent was evaporated, the residue was chromatographed on a column of silica gel to give 0080 90 mg. Yield 80%. $^1$H NMR(100 MHz, $CD_3OD$) δ 2.8(s, 3H), 6.7(s, 1H), 7.6(d, 1H), 8.4(dd, 1H), 8.7(s, 1H), 8.9(d, 1H), 9.2(s, 1H).

Synthesis of 0110. 80 mg 0079 was dissolved in 20 ml of dry THF. To this solution 180 mg of 3,5-dimethoxyl-4-isopropyl benzoyl chloride was added and 100 mg of triethylamine was added dropwise while stirring. The resulting solution was stirred at room temperature for half an hour. Product was extracted with ethyl acetate and washed with water. After the solvent was evaporated, the residue was dissolved in 5 ml of dichloromethane and to this solution, 100 mg $BBr_3$ was added at −78° C. This solution was stirred overnight at room temperature, then 100 ml water was added and the product was extracted with ethyl acetate and dried on sodium sulfate. After solvent was evaporated, the residue was chromatographed on a column of silica gel to give 0110 50 mg. Yield 40%. $^1$H NMR (100 MHz, $CDCl_3$), δ 1.24 (d, 3H), 1.26(d, 3H), 3.1(multi, 1H), 2.75(s, 3H), 6.6(s, 1H), 6.95(s, 2H), 8.3(s, 1H).

Synthesis of 0093. The compound 0093 was synthesized from 0092 by the same method as the synthesis of 0021. It is a dark green powder.

Synthesis of 0096. 100 mg 0093 was dissolved in 20 ml of dry THF. To this solution 180 mg of 3,5-dimethoxyl-4-isopropyl benzoyl chloride was added and 100 mg of triethylamine was added dropwise while stirring. The resulting solution was stirred at room temperature for half an hour. Product was extracted with ethyl acetate and washed with water. After solvent was evaporated, the residue was dissolved in 5 ml of dichloromethane and to this solution, 100 mg $BBr_3$ was added at −78° C. This solution was stirred overnight at room temperature, then 100 ml water was added and the product was extracted with ethyl acetate and dried on sodium sulfate. After solvent was evaporated, the residue was chromatographed on a column of silica gel to give 0096 60 mg. Yield 43%. $^1$H NMR (100 MHz, $CDCl_3$), δ 1.24(d, 6H), 1.26(d, 6H), 3.05 (multi, 2H), 6.88(s, 1H), 6.98(s, 2H), 7.3(s, 4H).

Synthesis of 0102. 0021 100 mg, 3,5-diacetoxy-4-isopropyl benzoic acid 80 mg and DCC 80 mg were added in 10 ml dry dichloromethane. This solution was stirred for 2 hours at room temperature. After purification by column chromatographer, the product was dissolved in 20 ml methanol. To this solution, a solution of 50 mg sodium carbonate in 2 ml water was added and the resulting solution was stirred at 50° C. for 4 hour. Product was extracted with ethyl acetate and washed with water and purified by column to give 0102 30 mg. Yield: 16%. $^1$H NMR (100 MHz, $CDCl_3$), δ 1.24(d, 6H), 1.26(d, 6H), 3.1(multi, 1H), 3.75(s, 3H), 3.85(s, 3H), 6.6(s, 1H), 6.62(multi, 2H), 6.95(s, 2H), 7.2(d, 1H), 8.3(s, 1H).

Synthesis of 0104. The compound 0104 was synthesized from 0103 by the same method as the synthesis of 0021. It's also a dark green powder.

Synthesis of 0107. The compound 0107 was synthesized from 0104 by the same method as the synthesis of 0096. Yield 52%. $^1$H NMR (100 MHz, $CDCl_3$), δ 1.25(d, 3H), 1.27(d, 3H), 3.05(multi, 1H), 5.02(s, 2H), 6.6(s, 1H), 6.95(s, 2H), 7.1(s, 5H), 8.4(s, 1H).

Synthesis of 0113. The compound 0113 was synthesized by the reaction of 0104 and 2-thiophenecarbonyl chloride by the same method of synthesis as BLI-081. Yield: 90%. $^1$H NMR (100 MHz, $CDCl_3$), δ 5.05(s, 2H), 6.85(s, 1H), 7.2(dd, 1H), 7.25(s, 5H), 7.6(d, 1H), 7.8(d, 1H), 8.3(s, 1H).

Synthesis of 0116. The compound 0116 was synthesized from 0104 by the same method of synthesis as 0066. Yield: 50% $^1$H NMR (100 MHz, $CDCl_3$), δ 2.5(multi, 4H), 3.6(s, 2H), 3.8(multi, 4H),), 4.9(s, 2H), 6.5(s, 1H), 7.12(s, 5H), 7.6(dd, 4H), 8.3(s, 1H).

Synthesis of 0120. The compound 0120 was synthesized from 0119, as a dark green powder by the same method as the synthesis as 0021.

Synthesis of 0122. The compound 0122 was synthesized from 0120 by the same method of synthesis as 0066. Yield: 55% $^1$H NMR (100 MHz, $CDCl_3$), δ 2.5(multi, 4H), 2.9(s, 3H), 3.6(s, 2H), 3.8(multi, 4H), 3.85(s, 3H), 3.9(s, 3H), 6.6(s, 1H), 6.7(multi, 2H), 7.2(d, 1H), 7.7(dd, 4H), 8.4

Synthesis of 0125. 100 mg 0093 was dissolved in 40 ml dry THF. While stirring thoroughly, 120 mg 3-chloromethyl benzoic chloride was added, then 100 mg triethylamine was added dropwise over 2 minutes. The reaction was completed in half an hour. Product was extracted with ethyl acetate and washed with water. After the solvent was evaporated the residue was dissolved in 2 ml of morpholine. This solution was stirred at 60° C. for 2 hours and water was added. Product was extracted with ethyl acetate and washed with water. After solvent was evaporated, the residue was chromatographed on a column of silica gel to give 0125 100 mg. Yield: 60%. $^1$H NMR (100 MHz, $CDCl_3$), δ 1.27(d, 6H), 2.6(multi, 4H), 3(multi, 1H), 3.65(s, 2H), 3.8(multi, 4H), 6.85(s, 1H), 7.4(s, 4H), 7.4-8.0(multi, 4H), 8.35(s, 1H).

Synthesis of 0126. The compound 0126 was synthesized from 0021 by the same method of synthesis as 0125. Yield: 60%. $^1$H NMR (100 MHz, $CDCl_3$), δ 2.55(multi, 4H), 3.6(s, 2H), 3.8(multi, 4H), 3.85(s, 3H), 3.9(s, 3H), 6.45(s, 1H), 6.6(multi, 2H), 7.25(d, 1H), 7.4-8.0(multi, 4H), 8.25(s, 1H).

Synthesis of 0128. The compound 0128 was synthesized from 0093 by the same method of synthesis as 0080. Yield: 80%. $^1$H NMR (100 MHz, $CDCl_3$), δ 1.26(d, 6H), 3.0(multi, 1H), 7.02(s, 1H), 7.35(s, 4H), 7.8(s, 1H), 8.7(s, 1H), 9.0(s, 1H), 9.2(s, H), 9.4(s, 1H).

Synthesis of 0135. The compound 0135 was synthesized from 0104 by the same method of synthesis as 0080. Yield: 82%. $^1$H NMR(100 MHz, $CDCl_3$) δ 4.1(s, 2H), 6.7(s, 1H), 7.25(s, 5H), 7.6(d, 1H), 8.4(dd, 1H), 8.7(s, 1H), 8.9(d, 1H), 9.2(s, 1H).

Synthesis of 0136. 100 mg 0104 was dissolved in 40 ml dry THF. While stirring thoroughly, 120 mg 3-chloromethyl benzoic chloride was added then 100 mg triethylamine was added dropwise over 2 minutes. The reaction was completed in half an hour. Product was extracted with ethyl acetate and washed with water. After the solvent was evaporated the residue was dissolved in 2 ml of N-methyl piperazine. This solution was stirred at 60° C. for 2 hours and water was added. Product was extracted with ethyl acetate and washed with water. After solvent was evaporated, the residue was chromatographed on a column of silica gel to give 0136 115 mg Yield: 70%. $^1$H NMR(100 MHz, CD$_3$OD) δ 4.1(s, 2H), 6.7(s, 1H), 7.25(s, 5H), 7.6(d, 1H), 8.4(dd, 1H), 8.7(s, 1H), 8.9(d, 1H), 9.2(s, 1H).

Synthesis of 0137. 100 mg 0104 was dissolved in 40 ml dry THF. While stirring thoroughly, 120 mg 3-chloromethyl benzoic chloride was added, then 100 mg triethylamine was added dropwise over 2 minutes. The reaction was completed in half an hour. Product was extracted with ethyl acetate and washed with water. After the solvent was evaporated the residue was dissolved in 2 ml morpholine. This solution was stirred at 60° C. for 2 hours and water was added. Product was extracted with ethyl acetate and washed with water. After the solvent was evaporated, the residue was chromatographed on a column of silica gel to give 0137 130 mg Yield: 75%. $^1$H NMR(100 MHz, CD$_3$OD) δ 2.4(s, 3H), 2.6(s, 8H), 3.6(s, 2H), 5.05(s, 2H), 6.5(s, 1H), 7.35(s, 5H), 7.4-8.0(multi, 4H), 8.2(s, 1H).

EXAMPLE 5

Therapeutic Formulations

In one aspect, the invention provides a variety of therapeutic uses for the types of dithiolopyrrolones and the specific compounds disclosed. In various embodiments, compounds of the invention may be used therapeutically in formulations or medicaments for the treatment of human proliferative diseases, such as blood vessel proliferative disorders, and fibrotic disorders such as cancers, tumors, hyperplasias, fibrosis, angiogenesis, psoriasis, atherosclerosis and smooth muscle cell proliferation in the blood vessels, such as stenosis or restenosis following angioplasty, including cancers susceptible to compounds of the invention (such as susceptible solid tumors). The invention provides corresponding methods of medical treatment, in which a therapeutic dose of a compound of the invention is administered in a pharmacologically acceptable formulation. Accordingly, the invention also provides therapeutic compositions comprising compounds of the invention and a pharmacologically acceptable excipient or carrier. The therapeutic composition may be soluble in an aqueous solution at a physiologically acceptable pH.

The invention provides pharmaceutical compositions (medicaments) containing (comprising) compounds of the invention. In one embodiment, such compositions include compounds of the invention in a therapeutically or prophylactically effective amount sufficient to alter, and preferably inhibit, pathological cellular proliferation (proliferative disease), and a pharmaceutically acceptable carrier.

The compounds of the invention may be used in combination with other compositions and procedures for the treatment of diseases. For example, a tumor may be treated conventionally with photodynamic therapy, surgery, radiation or chemotherapy combined with a compounds of the invention, and then compounds of the invention may be subsequently administered to the patient to extend the dormancy of micrometastases and to stabilize and inhibit the growth of any residue primary tumor.

A "therapeutically effective amount" refers to an amount effective, at dosages and for periods of time necessary, to achieve the desired therapeutic result, such as growth reduction or elimination of a proliferative disease in the case of cancers. A therapeutically effective amount of a compound of the invention may vary according to factors such as the disease state, age, sex, and weight of the individual, and the ability of the compound of the invention to elicit a desired response in the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Dosage unit form, as used herein, refers to physically discrete units suited as unitary dosages; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. A therapeutically effective amount is also one in which any toxic or detrimental effects of the compound of the invention are outweighed by the therapeutically beneficial effects.

A "prophylactically effective amount" refers to an amount that is effective, at dosages and for the periods of time necessary, to achieve the desired prophylactic result, such as preventing or inhibiting the rate of metastasis of a tumour or the onset of intimal hyperplasia. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of a compounds of the invention may be 0.1 nM-0.1M, 0.1 nM-0.05M, 0.05 nM-15 µM or 0.01 nM-10 µM. Alternatively, the total daily dose may range from about 0.001 to about 1,000 mg/kg of a patient's body mass. Dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the methods of the invention.

As used herein "pharmaceutically acceptable carrier" or "diluent" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride, and the like, in the composition. Prolonged absorption of the injectable compositions can be brought about by including in the composition an agent which delays absorption, for example, monostearate salts and gelatin. Moreover, the compounds of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound of the invention may be formulated with one or more additional compounds that enhance the solubility of the compound of the invention.

In accordance with another aspect of the invention, therapeutic compositions of the present invention, comprising compounds of the invention, may be provided in containers having labels that provide instructions for use of compounds of the invention to treat proliferative diseases, including cancers and psoriasis.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range.

What is claimed is:

1. A method of treating leukemia, non-small cell lung cancer, colon cancer, astrocytoma, glioblastoma, gliosarcoma, or melanoma comprising administering a therapeutically effective amount of a compound according to the formula:

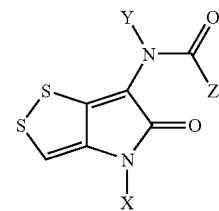

wherein X, Y and Z are defined as follows:

| Compound | X | Y | Z |
|---|---|---|---|
| 0058 | 2,4-dimethoxy-phenyl | H | 3,5-di-trifluoromethylphenyl. |

2. A method of treating ovarian cancer comprising administering a therapeutically effective amount of a compound according to the formula:

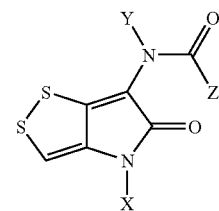

wherein X, Y and Z are selected from the following definitions:

| Compound | X | Y | Z |
|---|---|---|---|
| 0037 | 2,4-dimethoxy-phenyl | H | thiophene-2-methyl |
| 0058 | 2,4-dimethoxy-phenyl | H | 3,5-di-trifluoromethylphenyl |
| BLI-093 | 2,4-dimethoxy-phenyl | H | 4-trifluoromethylphenyl |
| WBL-007 | 2,4-dimethoxy-phenyl | H | 2-thiophenyl |
| WBL-018 | 2,4-dimethoxy-phenyl | H | 4-fluorophenyl |
| R3 | 2,4-dimethoxy-phenyl | H | 3,5-difluorophenyl |
| R4 | 2,4-dimethoxy-phenyl | H | 2,3,4-trifluorophenyl. |

3. A method of treating non-small cell lung cancer comprising administering a therapeutically effective amount of a compound according to the formula:

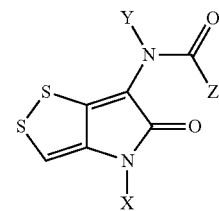

wherein X, Y and Z are selected from the following definitions:

| Compound | X | Y | Z |
|---|---|---|---|
| 0066 | 2,4-dimethoxy-phenyl | H | 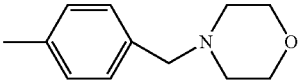 |
| 0068 | 2,4-dimethoxy-phenyl | H | 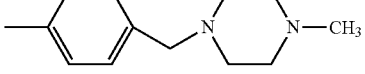 |
| 0069 | 2,4-dimethoxy-phenyl | H | 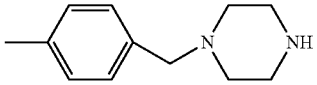 |
| 0136 | 2,4-dimethoxy-phenyl | H | 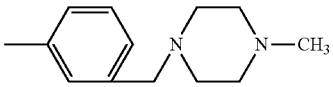 |
| WBI-4 | 4-isopropylphenyl | H | 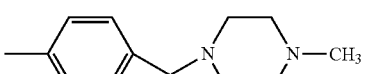 |
| WBI-6 | 2,4-dimethoxy-phenyl | H |  |
| WBI-5 | 4-isobutylphenyl | H | 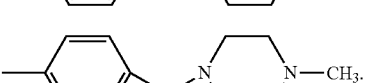 |

4. A method of treating renal cancer comprising administering a therapeutically effective amount of a compound according to the formula:

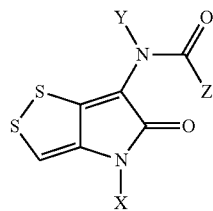

wherein X, Y and Z are defined as follows:

| Compound | X | Y | Z |
|---|---|---|---|
| 0058 | 2,4-dimethoxy-phenyl | H | 3,5-di-trifluoromethylphenyl. |

5. A method of treating prostate cancer comprising administering a therapeutically effective amount of a compound according to the formula:

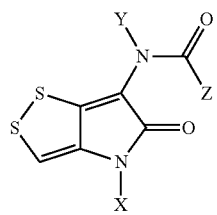

wherein X, Y and Z are defined as follows:

| Compound | X | Y | Z |
|---|---|---|---|
| 0058 | 2,4-dimethoxy-phenyl | H | 3,5-di-trifluoromethylphenyl. |

6. A method of treating breast cancer comprising administering a therapeutically effective amount of a compound according to the formula:

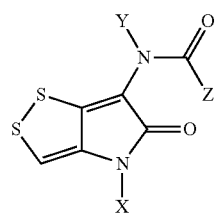

wherein X, Y and Z are defined as follows:

| Compound | X | Y | Z |
|---|---|---|---|
| 0058 | 2,4-dimethoxy-phenyl | H | 3,5-di-trifluoromethylphenyl. |

* * * * *